US009829005B2

(12) United States Patent
Jactat et al.

(10) Patent No.: US 9,829,005 B2
(45) Date of Patent: Nov. 28, 2017

(54) CENTRIFUGAL COMPRESSOR PROVIDED WITH A MARKER FOR MEASURING WEAR AND A METHOD OF MONITORING WEAR USING SAID MARKER

(71) Applicant: TURBOMECA, Bordes (FR)

(72) Inventors: Paul-Etienne Jactat, Pau (FR); Pascal Lebrusq, Idron (FR); Jerome Sarramea, Urrugne (FR); Lionel Scuiller, Billere (FR)

(73) Assignee: TURBOMECA, Bordes (FR)

( * ) Notice: Subject to any disclaimer, the term of this patent is extended or adjusted under 35 U.S.C. 154(b) by 723 days.

(21) Appl. No.: 14/349,168

(22) PCT Filed: Sep. 27, 2012

(86) PCT No.: PCT/FR2012/052189
§ 371 (c)(1),
(2) Date: Apr. 2, 2014

(87) PCT Pub. No.: WO2013/050688
PCT Pub. Date: Apr. 11, 2013

(65) Prior Publication Data
US 2015/0086334 A1 Mar. 26, 2015

(30) Foreign Application Priority Data

Oct. 7, 2011 (FR) ...................... 11 59071

(51) Int. Cl.
*F04D 27/00* (2006.01)
*F04D 29/42* (2006.01)
(Continued)

(52) U.S. Cl.
CPC ........... *F04D 27/001* (2013.01); *F04D 17/08* (2013.01); *F04D 29/4206* (2013.01); *G01N 3/56* (2013.01);
(Continued)

(58) Field of Classification Search
CPC ...... F01D 11/12; F01D 11/122; F01D 11/127; F04D 27/001; F04D 17/08; G01N 3/56
See application file for complete search history.

(56) References Cited

U.S. PATENT DOCUMENTS

| 3,575,427 A * | 4/1971 | Lapac | F01D 11/12 277/414 |
| 3,580,692 A * | 5/1971 | Mikolajczak | F01D 11/127 415/13 |
| 4,329,308 A * | 5/1982 | Langer | F01D 11/122 264/162 |
| 4,466,772 A * | 8/1984 | Okapuu | F01D 11/08 415/171.1 |

(Continued)

FOREIGN PATENT DOCUMENTS

| FR | 2 938 651 | 5/2010 | |
| FR | WO 2010055263 A1 * | 5/2010 | ............. F01D 5/005 |
| FR | 2 942 267 | 8/2010 | |

OTHER PUBLICATIONS

English Translation of WO 2010055263A1.*
International Search Report dated Feb. 1, 2013 in PCT/FR12/052189 Filed Sep. 27, 2012.

*Primary Examiner* — Mark Laurenzi
*Assistant Examiner* — Shafiq Mian
(74) *Attorney, Agent, or Firm* — Oblon, McClelland, Maier & Neustadt, L.L.P.

(57) ABSTRACT

A device and method for precise measurement of erosion of compressors, without removing an engine, and with easy positioning. A centrifugal compressor of a gas turbine with a radial air inlet includes an impeller including blades and a casing for an air stream to flow in the blades of the impeller. The casing, covered with an abradable coating, includes an annular elbow zone in a substantially median part. Marking depressions of predetermined depths, preferably in groups, are machined in the abradable coating of the zone. Examinations by endoscopy are successively performed to provide an image signal of the markers. Processing the endoscopic signal supplies a number of remaining markers and a crite- (Continued)

rion for decision on removing the engine is applied thereto. Erosion occurs in the elbow of the casing and evolution thereof may enable monitoring of erosion of other components of the compressor, in particular the blades of the impeller.

9 Claims, 3 Drawing Sheets

(51) Int. Cl.
*F04D 17/08* (2006.01)
*G01N 3/56* (2006.01)

(52) U.S. Cl.
CPC .... *F05D 2220/329* (2013.01); *F05D 2220/40* (2013.01); *F05D 2260/80* (2013.01)

(56) References Cited

U.S. PATENT DOCUMENTS

| | | | | |
|---|---|---|---|---|
| 4,652,209 | A | * | 3/1987 | Buddenbohm .......... F01D 11/12 415/174.4 |
| 5,472,315 | A | * | 12/1995 | Alexander .............. C23C 24/08 415/173.4 |
| 5,975,845 | A | | 11/1999 | Ball |
| 9,249,680 | B2 | * | 2/2016 | Lee ....................... F01D 11/122 |
| 2003/0175116 | A1 | * | 9/2003 | Le Biez ................... F01D 5/20 415/173.4 |
| 2006/0110247 | A1 | * | 5/2006 | Nelson ................... F01D 11/12 415/173.4 |
| 2010/0014956 | A1 | * | 1/2010 | Guemmer ............ F04D 29/685 415/9 |
| 2010/0098536 | A1 | * | 4/2010 | Guemmer ............ F04D 29/164 415/208.1 |
| 2011/0299987 | A1 | | 12/2011 | Billotey et al. |

* cited by examiner

US 9,829,005 B2

CENTRIFUGAL COMPRESSOR PROVIDED WITH A MARKER FOR MEASURING WEAR AND A METHOD OF MONITORING WEAR USING SAID MARKER

TECHNICAL FIELD

The invention relates to a centrifugal compressor of a gas turbine, provided with a marker for monitoring wear, as well as a method of measuring wear on a centrifugal compressor using such a marker.

The invention applies in particular to the turboshaft engines of helicopters, in particular turboshaft engines with single-stage or two-stage compressors.

Wear by erosion affects the main components of the air flow path of an engine equipped with at least one centrifugal compressor with a radial air inlet. The parts of the compressor, and the zones of these parts that are most exposed to erosion, are respectively: the impeller, in particular the leading edges of the main blades; the radial diffuser, in particular the leading edges of its blades; and the casing of the impeller, in particular in the region of the elbow of the casing.

The invention relates more generally to the field of monitoring the effective functioning of a turbine, said monitoring necessitating the detection of the erosion caused generally by ingesting foreign bodies in the flow path, in particular sand.

PRIOR ART

A known solution is to measure the erosion of a compressor on the leading edge of the main blades of the impeller, in particular by endoscopy. The patent document FR 2 938 651 describes such a method of measuring wear of the leading edge of a rotary impeller blade. A permanent marker is produced at a predetermined distance from the leading edge, and this distance is monitored by an endoscope positioned in a field of view including the marker and a part of the leading edge. Means for processing the images provided by the endoscope make it possible to deduce the position of the leading edge with respect to the marker.

However, the measurement of the retreat of the leading edges of the main blades of the impeller is marred by substantial imprecision, and access to the blades is difficult without removing the engine. In addition, the positioning of an indicator on rotary parts is difficult to implement because of high stresses on the impeller in operation. Furthermore, there is no reliable reference for measuring the position of the indicator with respect to a leading edge of a blade when the latter is fully subjected to erosion.

In general, these imprecisions in the characterisation of the wear on the parts may result in an erroneous diagnosis of the condition of the parts, and a premature or delayed removal of the engine. Such imprecision does not allow targeted maintenance of individual parts.

DESCRIPTION OF THE INVENTION

The invention aims to eliminate these drawbacks, in particular it aims to achieve a precise measurement of the erosion of compressors, without removing the engine, as well as easy positioning. In order to do this, although the wear on the compressor casings is not critical, which a priori is not an incentive to use them as markers, it has been noted that installing an indicator in the casing may be useful for characterising the wear. In fact, the elbow of casings erodes, and the monitoring of this erosion by an appropriate marker enables such characterisation of the wear, not only on the casings, but also on adjacent parts of the compressors, in particular impeller blades.

More precisely, the invention relates to a centrifugal compressor of a gas turbine with a radial air inlet. Such a compressor includes an impeller provided with blades and a casing for the air stream in the blades. The casing, which is covered with an abradable coating, has an annular elbow zone in a substantially median part. In this elbow zone, at least one marking depression of predetermined depth, known as a marker, is machined in the abradable coating. This compressor preferably constitutes the first compression stage of a single-stage, two-stage or multi-stage turboshaft engine.

According to advantageous features:
- at least two, preferably at least three groups of at least two, preferably at least three markers are distributed along the elbow zone of the casing;
- the markers of each group have different and quantified initial depths;
- the markers of each group may be aligned in said elbow zone and the installation thereof can be chosen between a meridian, a radius and a line inclined between the meridian and the radius;
- the markers have a shape chosen from among a cylindrical shape, preferably a bore with a base which is circular or oblong, a spherical segment, of conical shape, and grooving.

The invention also relates to a method of monitoring wear on a centrifugal compressor of the type described above. In this method:
- at least one marker is produced by machining at least one depression of a predetermined depth in the abradable coating of the elbow of the casing;
- examinations by endoscopy are successively performed over time;
- for each examination, an endoscope is introduced into the compressor and an active end of the endoscope is positioned facing the marker(s) in order to provide an image signal of the markers;
- processing the endoscopic signal supplies a number of remaining markers and a criterion for decision on removing the engine is applied as a function of this number and of comparative wear data.

According to preferred embodiments:
- markers have different depths, and the difference between the closest two depths is quantified according to a calibrated degree of advance of wear;
- the markers are regularly distributed over the circumference of the elbow of the casing, individually or in groups of at least two markers, preferably at least three;
- a comparison between the counts of remaining markers during successive examinations supplies a measurement of the speed of erosion and progress of the wear on the casing as well as, by extrapolating from stored data relating to correlations of wear between the compressor parts, that of the other parts of the compressor;
- for each examination, the decision criterion compares the number of remaining markers with a critical number established as a function of the stored data, and the engine is removed for the replacement of the worn parts when the critical number is reached.

DESCRIPTION OF THE DRAWINGS

Other data, characteristics and advantages of the present invention will become apparent by reading the following description, which is not limited, with reference to the appended drawings, in which, respectively.

DETAILED DESCRIPTION

Figure 1:
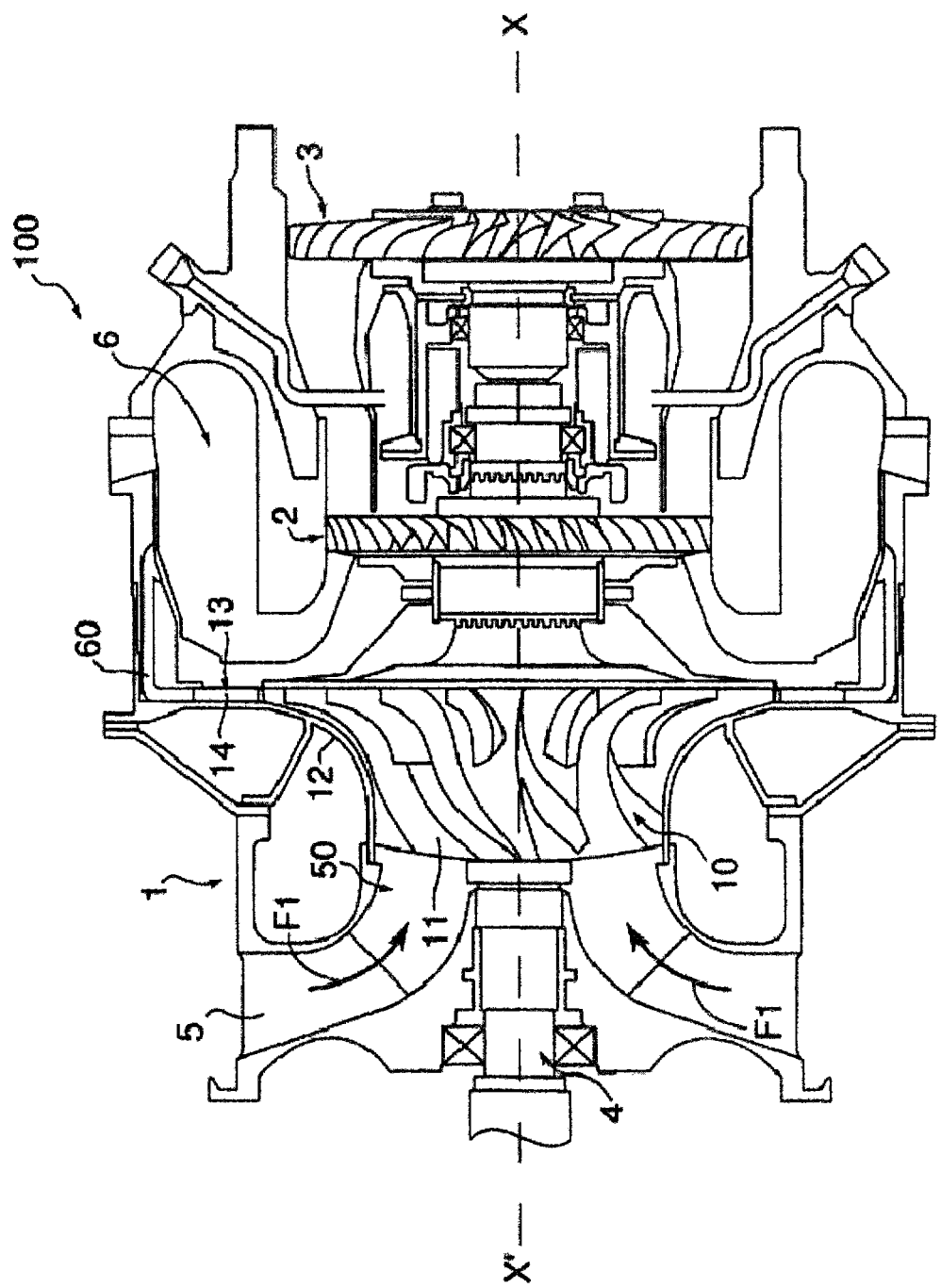
FIG. 1 shows a partial sectional view of a helicopter turboshaft engine including a compressor according to the invention.

The turboshaft engine 100 illustrated by the sectional view in FIG. 1 includes, substantially axially symmetrically about the central axis X'X: a centrifugal compressor 1; turbines 2 and 3 for driving the compressor 1 and power axes of the helicopter (propeller, transmission housing, etc.) via a through shaft 4; a radial inlet 5 of a sleeve 50 for circulating a fresh air stream F1, and a combustion chamber 6.

More precisely, the centrifugal compressor 1 principally comprises a compression impeller 10 provided with blades 11 and supplied with air F1, a casing 12 limiting an annular channel in which the air stream F1 flows, and a radial diffuser 13 with fins 14.

In operation, the air stream F1 is first drawn into the fresh air inlet 2, then compressed between the blades 11 of the impeller and the casing 12. The compressed air flow F1 then exits radially from the impeller 10.

The air stream F1 then passes through the diffuser 13 formed on the periphery of the compressor 1, in order to be straightened by the curved blades and transported towards inlet channels 60 of the combustion chamber 6.

In operation, the air stream F1 which contains foreign particles, for example grains of sand, will erode the main parts of the compressor: the rotary blades 11 of the impeller, the casing 12 and the blades 14 of the diffuser.

Figure 2:
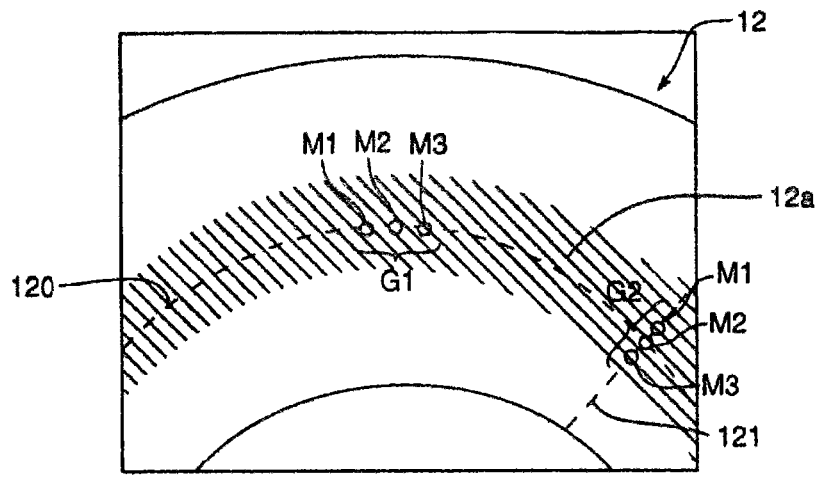
FIG. 2 shows a partial axial view of a casing according to the invention including two groups of three markers aligned on a radius and on a meridian of the elbow of the casing.

In order to measure the progress of this erosion, the casing 12 is machined in order to produce marker depressions 14 as illustrated by FIG. 2. The casing 12 has in its central part an annular zone forming an elbow 12a. A first group G1 of three markers M1, M2, and M3 have been machined in this elbow 12a. The markers of the group G1 are aligned on a meridian 120 (represented by dotted lines) of the elbow 12a. Another example of alignment of the markers M1 to M3 is also illustrated. In this alignment, the markers M1 to M3 form a group G2 along a radius 121 (represented by dotted lines) of the elbow 12a.

In this case, the markers have a cylindrical shape with a circular base. Alternatively, other shapes are possible: a bore with an oblong base, a spherical segment, a conical shape, or grooving.

In general, the markers of one and the same group are sufficiently close together, less than 10 mm apart, to be able to undergo the same type of erosion. In addition, the markers have a maximum aperture of less than approximately 1 mm so as not to be blocked by the ingestion of foreign bodies, in particular grains of sand.

The casing 12 is covered by a coating of a known abradable material, with a thickness of several millimetres, in order to avoid contact with the blades which would be detrimental to effective operation. The markers are machined in this abradable material.

However, the casing is the part which is eroded by the air stream F1 and in particular the elbow 12a. In FIG. 2, the elbow 12a forms an eroded zone shown shaded in relation to the rest of the elbow. The wear on the casing and the elbow thereof in particular does not affect the effective functioning of the engine.

Figure 3:
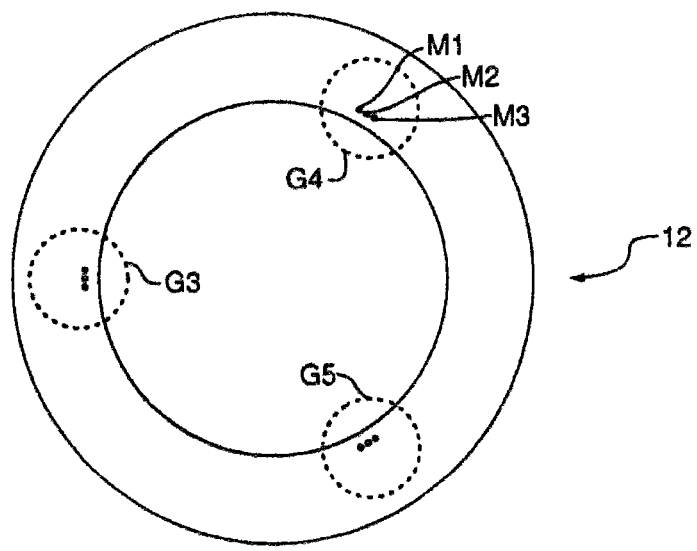
FIG. 3 shows a general axial view of an example of a casing according to the invention including three groups of three markers aligned on a meridian.

With reference to the general axial view in FIG. 3, an example of a casing 12 according to the invention includes three groups G3 to G5 of three markers each, identical to the previously described markers M1 to M3. The markers are aligned on the meridian 120 and the groups G3 to G5 are regularly distributed at 120° over the circumference of the elbow 12a of the casing 12. Alternatively, the markers M1 to M3 can be aligned on a radius 121 as illustrated in FIG. 2.

Figure 4:
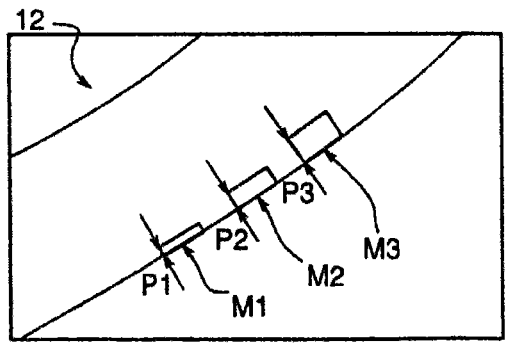
FIGS. 4 and 5 show sectional and perspective views of three markers of one of the preceding groups.
Figure 5:
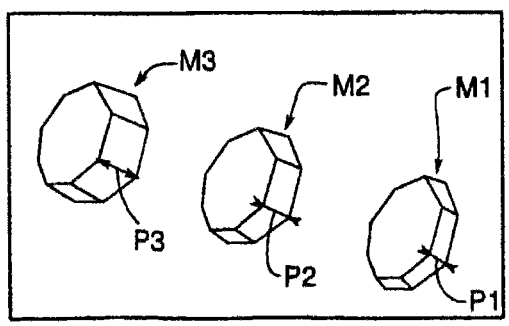

In the example, the markers have a substantially cylindrical shape and have different depths. The sectional and perspective views in FIGS. 4 and 5 show more precisely the three markers M1 to M3 and the different depths P1 to P3 thereof. The markers are cylindrical with polyhedral walls. They succeed one another with an increasing depth. The difference in depth between two adjacent markers is constant and quantified: it corresponds to a calibrated unit of advance of the wear. In the example, the depth quantum is 0.2 mm and the depths of the markers M1 to M3 are successively equal to 0.2, 0.4 and 0.6 mm. During examinations of the casing—by endoscopy for example—the degree of advance of the wear on the casing is between 0 and 0.2 mm if no markers have disappeared, between 0.2 and 0.4 mm if the marker M1 has disappeared, and between 0.4 and 0.6 mm if the marker M2 disappears.

The disappearance of the marker M2 then leads to an inspection of the parts of the compressor in so far as such erosion of the casing signals, by extrapolation according to the type of engine and the use profile, critical erosion of the blades of the impeller. Such critical erosion corresponds to a limit of use which then necessitates a replacement of the eroded parts.

In order to refine the measurement of the state of wear of the casing and therefore of the other parts, a larger number of markers per group with a lower quantification of depth, for example 0.1 mm, can be implemented.

Figure 6:
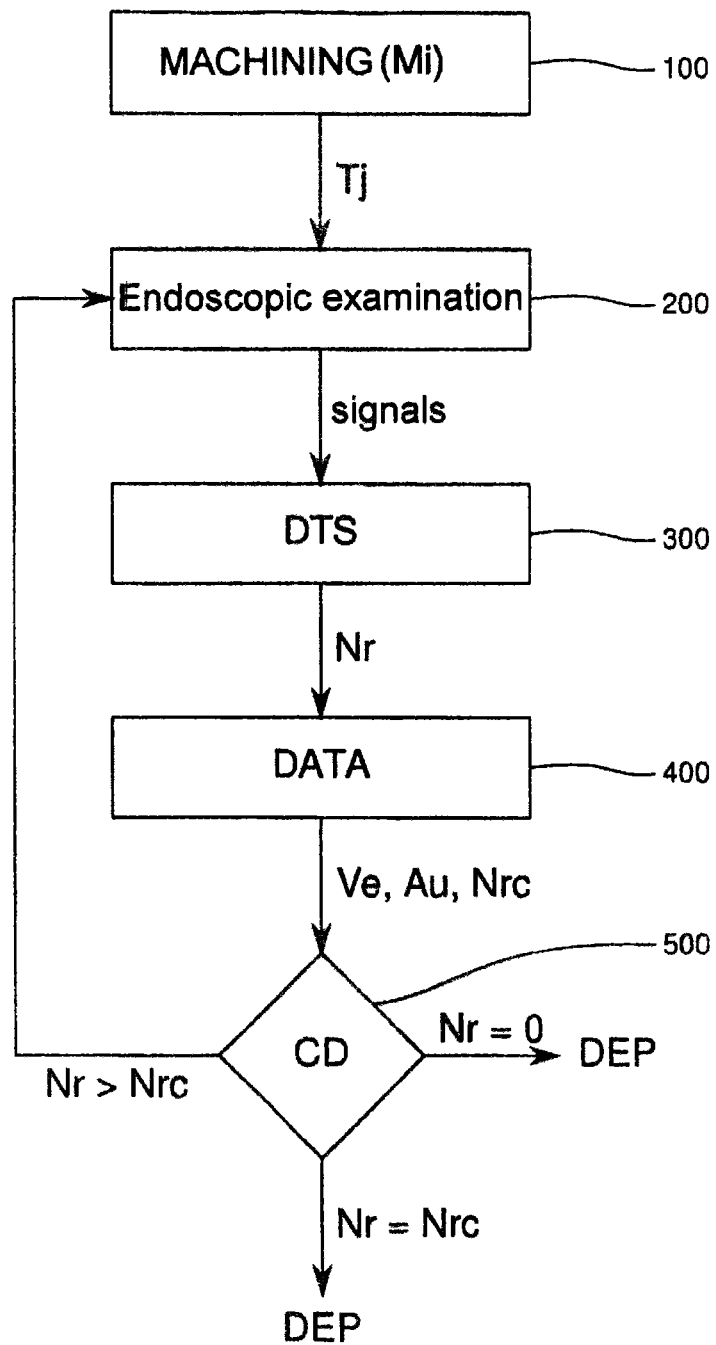
FIG. 6 shows an example of a flow diagram of the steps for implementing the method of measuring wear according to the invention.

The flow diagram in FIG. 6 illustrates an example of a succession of steps which can be implemented in the context of the method of monitoring the wear on a given compressor according to the invention. In this example, markings—such as the groups of markers G3 to G5 comprising "i" markers Mi, "i" being equal to or greater than 3, for example equal to 4 or 5—are machined in the abradable coating of the elbow of the casing (step 100). More generally, more than three groups can be machined.

Examinations by endoscopy are then performed successively over time (step 200), for example after each mission separated by durations Tj. For each examination, the endoscope is introduced into the compressor following intended routes until the active end of the endoscope reaches a position facing each of the three groups G3 to G5 in the example and supplies image signals of the markers Mi.

A device for processing the signal DTS receives the endoscopic signals. The device then establishes the number of remaining markers Nr per group (step 300) and applies a decision criterion CD for removing the engine as a function of this number. The result of this application is supplied to an operator.

During successive examinations over time, an erosion speed "Ve" and progress of the wear "Au" of the casing and the blades of the impeller are established by the device DTS on the basis of the number of remaining markers Nr and durations Tj. These data are also stored in the processing device (step 400).

In order to do this, data DATA are also stored in the processing device relating to: the distribution of the erosion of the casing, the correlation of wear as a function of the configuration of the engines between the parts of the compressor making it possible to extrapolate that of the blades of the impeller from that of the casing, the profiles of the helicopter missions and the particle size of the foreign bodies ingested as a function of missions, the prior "Ve" and "Au" results relating to the engine examined as well as the "Ve" and "Au" results of engines as a function of their conditions of use.

The criterion CD establishes a critical number of remaining markers "Nrc" and then interprets, as a function of the data DATA and the critical number of markers "Nrc", the number of remaining markers "Nr" per group G3 to G5 in terms of the wear on parts, in particular the blades of the impeller, (step 500). For example, it may be that only the number of markers of the group G2 is critical. As long as this number is at least equal to two for the group G4, it is not necessary to remove the engine, even if the other groups G3 and G5 have a number of markers equal to one during an examination. Thus, for each engine, a critical number of remaining markers "Nrc", at least equal to one, is established for each group of markers.

During each examination, the number of remaining markers "Nr" per group G3 to G5 is predetermined. If this number "Nr" is equal to zero for at least one group, the decision criterion calls for the immediate removal of the engine "DEP" and the changing of the parts of the compressor exposed to wear (casing, blades of the impeller, fins of the diffuser). If the number Nr is equal to Nrc for the group in question, the removal is also decided on.

Alternatively, the markers may not be distributed in groups, but for example regularly distributed along a meridian of the elbow. In this case, the number Nrc is simply equal to 1, unless the speed "Ve" or the advance of wear Au increases substantially: the number Nrc then becomes 2 in order to avoid any delayed replacement of components.

The invention is not limited to the embodiments described and illustrated. Thus the markers may not be aligned with depressions in one and the same group, for example in accordance with the arrangements in a V, in a triangle, in a square, etc.

The invention claimed is:

1. A centrifugal compressor of a gas turbine with a radial air inlet, comprising:
   an impeller including vanes; and
   a casing for delimiting a flow of an air stream in the vanes,
   a central part of the casing including an annular zone forming an elbow,
   wherein the casing is covered with an abradable coating,
   wherein a marking depression of a predetermined depth as a marker is machined in the abradable coating in the annular zone forming the elbow, the marker includes a face and walls connecting a surface of the abradable coating to the face of marker, and a distance between the surface of the abradable coating and the face of the marker is equal to the predetermined depth,
   wherein the casing includes two groups, each group including two markers, the groups of markers being distributed along the annular zone forming the elbow of the casing, the groups of markers being distributed at a predetermined distance from each other, and
   wherein the markers of each group have different and quantified predetermined depths.

2. A centrifugal compressor according to claim 1, wherein the markers of each group are aligned in the annular zone forming the elbow, and installation of the markers of each group is chosen between a meridian, a radius, and a line inclined between the meridian and the radius.

3. A centrifugal compressor according to claim 2, wherein the markers of a same group are less than 10 mm apart to be configured to undergo a same type of erosion.

4. A centrifugal compressor according to claim 1, wherein the marker has a maximum aperture of less than 1 mm so as not to be blocked by ingestion of foreign bodies, or ingestion of grains of sand.

5. A centrifugal compressor according to claim 1, wherein the marker has a shape chosen from among a cylindrical shape, or a bore with a base which is circular or oblong, a spherical segment, a conical shape, and a grooving.

6. A method of monitoring wear on a centrifugal compressor, the method comprising:
   providing a casing with a central part of the casing including an annular zone forming an elbow, the casing being covered with an abradable coating;
   producing at least two markers by machining depressions of a predetermined depth in the abradable coating of the annular zone forming the elbow of the casing, each of the at least two markers including a face and walls connecting a surface of the abradable coating to the face of each of the markers, and a distance between the surface of the abradable coating and the face of the marker is equal to the predetermined depth;
   performing examinations by endoscopy successively over time;
   introducing, for each examination, an endoscope into the compressor, and positioning an active end of the endoscope facing each of the at least two markers to provide an image signal of each of the at least two markers;
   processing the image signal to determine a number of remaining markers; and
   applying a criterion for decision on removing the engine based on the number of remaining markers and comparative wear data,
   wherein the markers have different depths and a difference between closest two depths is determined according to a calibrated degree of advance of wear.

7. A method of monitoring wear according to claim 6, wherein the markers are distributed over a circumference of the annular zone forming the elbow of the casing at a predetermined distance from each other.

8. A method of monitoring wear according to claim 6, wherein a comparison between the number of remaining markers during successive examinations supplies a measurement of a speed of erosion and progress of wear on the casing and other parts of the compressor, based on extrapolating stored data relating to correlations of wear between parts of the compressor.

9. A method of monitoring wear according to claim 8, wherein for each examination, the decision criterion compares the number of remaining markers with a critical number established as a function of stored data, and an engine is removed for replacement of the worn parts when the critical number is reached.

* * * * *